United States Patent
Torrent-Parker et al.

(10) Patent No.: US 7,968,109 B2
(45) Date of Patent: Jun. 28, 2011

(54) LIQUID COMPOSITIONS FOR TREATING PLANT PROPAGATION MATERIALS

(75) Inventors: Marlene Torrent-Parker, Singapore (SG); Kiran Shetty, Greensboro, NC (US)

(73) Assignee: Syngenta Crop Protection Inc., Greensboro, NC (US)

( * ) Notice: Subject to any disclaimer, the term of this patent is extended or adjusted under 35 U.S.C. 154(b) by 497 days.

(21) Appl. No.: 11/993,976

(22) PCT Filed: Jun. 28, 2006

(86) PCT No.: PCT/US2006/025187
§ 371 (c)(1),
(2), (4) Date: Jul. 2, 2008

(87) PCT Pub. No.: WO2007/005470
PCT Pub. Date: Jan. 11, 2007

(65) Prior Publication Data
US 2008/0318881 A1    Dec. 25, 2008

Related U.S. Application Data

(60) Provisional application No. 60/695,143, filed on Jun. 29, 2005.

(51) Int. Cl.
*A01N 25/00* (2006.01)
*A01N 25/26* (2006.01)
(52) U.S. Cl. ........ 424/405; 504/100
(58) Field of Classification Search ........ None
See application file for complete search history.

(56) References Cited

U.S. PATENT DOCUMENTS

| | | |
|---|---|---|
| 2003/0064119 A1 | 4/2003 | Emerson |
| 2004/0151750 A1 | 8/2004 | O'Leary et al. |
| 2004/0209923 A1 | 10/2004 | Berger et al. |
| 2005/0043182 A1 | 2/2005 | Douglass et al. |

OTHER PUBLICATIONS

Passam et al, "Wound Repair in Yam Tubers: Physiological Processes During Repair", New Phytology Journal, v. 77, abstract (1976).

*Primary Examiner* — Elli Peselev
(74) *Attorney, Agent, or Firm* — James Cueva

(57) ABSTRACT

The present invention includes a fast-drying liquid composition comprising a least one fungicide and at least one insecticide. The present invention further includes a method for treating plant propagation materials, especially cut seeds, including tubers, against pest, a method for promoting suberization in cut seeds, a method for decreasing the drying time of a liquid pesticide on cut seeds, and a method for selectively loading a pesticide onto the skin side of a cut seed.

22 Claims, No Drawings

LIQUID COMPOSITIONS FOR TREATING PLANT PROPAGATION MATERIALS

This application is a National Stage Entry under 35 USC §371 of International application serial number PCT/2006/025187, filed on Jun. 28, 2006, which claims priority to U.S. provisional application Ser. No. 60/695,143, filed on Jun. 29, 2005, now abandoned.

The present invention relates to liquid compositions and methods for treating plant propagation materials to protect against pest infestation in useful crops. More specifically, the present invention relates to methods for protecting crops against insects and fungi comprising applying to the plant propagation material an effective amount of a fast-drying liquid composition. The present invention further relates to plant propagation materials treated by said liquid compositions and to methods for promoting suberization in cut plant propagation materials. The present invention also relates to methods for speeding the drying time of plant propagation materials treated by liquid compositions.

Seed treatments are used on a large variety of crops to control many types of pests. Seed treatments are commonly used to ensure uniform stand establishment by protecting against soil borne diseases and insects. Systemic seed treatments may provide an alternative to traditional broadcast sprays of foliar fungicides or insecticides for certain early season airborne diseases and insects.

Many seed treatment materials are available for on-farm use. Some are known as hopper-box or planter-box treatments wherein liquid or dry formulations are applied to seed as it passes through an auger from the transport bin or truck to the planter boxes. These formulations are a very convenient way to apply seed treatment onto bulk seed right before planting. However, some seeds are treated and stored for later planting. Conventional dry treatments generally are formulated with talc or graphite which adhere the treatment chemical to the seed. Liquid seed treatments are less common due to the development of moisture-related problems such as fungal growth during storage. Good seed coverage is required for maximum benefit from any seed treatment formulation.

However, obtaining thorough seed coverage can be difficult when attempting to treat seed. For example, dry formulations can present unacceptable worker exposure to the fungicidal and insecticidal active ingredients. In addition to the increased risk of inhalation of dry formulations, it is often necessary to use larger quantities of dry formulations to achieve adequate seed coverage. Certain liquid formulations can become inhomogeneous on storage, such that particle sizes or viscosity do not remain constant. Additional problems can arise such as unacceptable drying times, material build-up in the seed treater, low seed flowability, poor seed coverage and dust-off of the active ingredients from the seed prior to planting. As a result, handling is rendered difficult and the biological efficacy of the seed treatment is reduced.

These problems are especially prominent in certain types of seeds. For example, tubers and bulbs, which may be planted whole or cut, require special care during seed treatment. In the case of tubers, such as potatoes, the cut portions of the potato seedling are especially vulnerable to bacterial and fungal infections because of the exposed surface of the potato. Potato tubers are easily skinned, nicked, and bruised during handling operations, causing seed damage which may affect plant growth. Because of this vulnerability, dust formulations are usually preferable for cut seed as liquid dip treatments may inhibit wound healing or suberization. Additionally, liquid treatments do not dry quickly enough to prevent fungal growth and bacterial spread during the time between cutting and planting.

There is a need in the art for alternative new liquid pesticidal compositions that dry quickly and are especially effective for use with cut seeds and other vulnerable plant propagation materials. More particularly, there is a need in the art for new liquid pesticidal treatments which promote wound healing or suberization on treated plant propagation materials.

The present invention includes a fast-drying liquid composition for treating plant propagation materials, especially cut seeds, including tubers, against pests and promoting suberization. More particularly, the present invention includes a fast-drying liquid formulation comprising at least one fungicide and at least one insecticide.

The present invention relates to a fast-drying liquid composition for treating and protecting plant propagation material. In one embodiment, the present invention relates to a fast-drying liquid composition comprising water, at least one fungicide, and at least one insecticide in combination with a blend of a drying agent, a wetting agent, a dispersing agent, a suberization agent, and optionally, an antifreeze agent and a solvent. The fast-drying liquid composition provides protection to the treated plant propagation material and dries within 90 minutes of application. The present invention also relates to a method for treating plant propagation material, including seeds, comprising applying the fast-drying liquid composition.

The present invention further relates to a method for preventing pest infestation in useful crops comprising treating plant propagation material, including seeds, with a pesticidally effective amount of a fast-drying liquid composition comprising water, at least one fungicide, and at least one insecticide in combination with a blend of a drying agent, a wetting agent, a dispersing agent, a suberization agent, and optionally, an antifreeze agent and a solvent.

The present invention also relates to a method for enhancing suberization in plant propagation material, including seeds, comprising treating the propagation material with an effective amount of a fast-drying liquid composition comprising water, at least one fungicide, and at least one insecticide in combination with a blend of a drying agent, a wetting agent, a dispersing agent, a suberization agent, and optionally, an antifreeze agent and a solvent.

The present invention further relates to a method for enhancing the drying time of plant propagation material treated by a liquid pesticide comprising applying a fast-drying liquid composition comprising water, at least one fungicide, and at least one insecticide in combination with a blend of a drying agent, a wetting agent, a dispersing agent, a suberization agent, and optionally, an antifreeze agent and a solvent.

The present invention also relates to plant propagation material treated with a fast-drying liquid composition comprising water, at least one fungicide, and at least one insecticide in combination with a blend of a drying agent, a wetting agent, a dispersing agent, a suberization agent, and optionally, an antifreeze agent and a solvent.

The present invention further relates to a method for selectively loading a liquid pesticide onto the skin side of a cut tuber, the method comprising treating the cut tuber with a fast-drying liquid composition comprising water, at least one fungicide, and at least one insecticide in combination with a blend of a drying agent, a wetting agent, a dispersing agent, a suberization agent, and optionally, an antifreeze agent and a solvent.

Fungicides and insecticides for use in treating seeds of useful plants are generally known, and processes for making them are described in The Pesticide Manual [Twelfth Edition, Editor: C. D. S. Tomlin]. For example and not for limitation, thiamethoxam, a neonicotinoid systemic insecticide useful for seed treatment, is described as entry number 792. Fludioxonil, a phenylpyrrole fungicide used in treating seeds of useful plants, is described as entry number 368.

The present invention includes a liquid formulation comprising at least one fungicide and at least one insecticide. The formulation is fast-drying, providing a dry treated seed within less than 90 minutes of treatment. More specifically, the liquid composition of the present invention comprises water, an effective amount of active ingredients containing at least one fungicide and at least one insecticide, and a blend of the following components, by weight:
  a. about 0.05-20% at least one wetting agent;
  b. about 0.05-10% at least one dispersing agent;
  c. about 0.05-5% at least one drying agent;
  d. about 0.01-20% at least one suberization agent; and, optionally
  e. about 0-20% antifreeze and optionally
  f. about 0-20% solvent.

Fungicides useful in the composition of the present invention include any agent useful for the prevention or treatment of fungal pests. Such fungicides may be particularly useful in controlling certain phytopathogenic fungi, and provide high fungicidal activity and relatively low phytotoxicity. The active ingredient mixtures according to the invention are effective against the following non-limiting classes of related phytopathogenic fungi: ascomycetes (e.g. *Venturia, Podosphaera, Erysiphe, Monilinia, Mycosphaerella, Uncinula, Leptosphaeria*); basidiomycetes (e.g. the genus *Hemileia, Rhizoctonia, Puccinia*); Fungi imperfecti (e.g. *Botrytis, Helminthosporium*, including *solani* (silver scurf), *Rhynchosporium, Fusarium, Septoria, Cercospora, Alternaria, Pyricularia* and in particular *Pseudocercosporella herpotrichoides*); oomycetes (e.g. *Phytophthora, Peronospora, Bremia, Pythium, Plasmopara*).

More specifically, fungicides useful in the composition of the present invention include, but are not limited to, diazole, triazole, phenylpyrrole, strobilurin, carboxamide, carboxanilide, especially ortho-substituted carboxanilide, carbamate, anilinopyrimidine, phenoxyquinoline, benzimidazole, systemic and phenylamide fungicides. More particularly, the present invention includes the use of systemic, strobilurin, and phenylpyrrole type fungicides. Even more particularly, the present invention includes the use of phenylpyrrole type fungicides.

Diazole fungicides that are useful in the present invention include imidazoles and pyrazoles. Examples of diazole fungicides that are useful include, without limitation, imazalil, oxpoconazole, pefurazoate, prochloraz, and trifulmizole. Mixtures of such diazoles can also be used.

Examples of triazole fungicides that are preferred for use in the present invention include, without limitation, amitrol, azaconazole, bitertanol, bromuconazole, climbazole, clotrimazole, cyproconazole, diclobutrazol, difenoconazole, diniconazole, diniconazole-M, epoxiconazole, etaconazole, fenbuconazole, fluquinconazole, fluotrimazole, flusilazole, flutriafol, furconazole, furconazole-cis, hexaconazole, imibenconazole, ipconazole, metconazole, myclobutanil, paclobutrazol, penconazole, propiconazole, quinconazole, simeconazole, tebuconazole, tetraconazole, triadimefon, triadimenol, triazbutil, triticonazole, and 1-(4-fluorophenyl)-2-(1H-1,2,4-triazole-1-yl)ethanone. Mixtures of such triazoles can also be used.

Examples of strobilurin-type fungicides that are useful in the present invention include, without limitation, azoxystrobin, dimoxystrobin, famoxadone, fluoxastrobin, kresoxim-methyl, metominostrobin, picoxystrobin, pyraclostrobin, and trifloxystrobin. Mixtures of strobilurin type fungicides can also be used. Mixtures of strobilurin-type fungicidies can also be used.

Examples of phenylpyrrole type fungicides that are useful in the present invention include, without limitation, fludioxonil and fenpiclonil. Mixtures of phenylpyrrole-type fungicidies can also be used.

Examples of amide and carboxamide type fungicides that are useful in the present invention include, without limitation, boscalide, carboxin, fenfuram, flutolanil, furametpyr, mepronil, oxycarboxin, mandipropamid, and thifluzamide. Mixtures of amide and carboxamide-type fungicidies can also be used.

Examples of carboxanilide type fungicides include, especially, ortho-substituted carboxanilide type fungicides. Fungicides in this class include, without limitation, 3-difluoromethyl-1-methyl-1H-pyrazole-4-carboxylic acid (2-bicyclopropyl-2-yl-phenyl)-amide and the isomers thereof; and 3-difluoromethyl-1-methyl-1H-pyrazole-4-carboxylic acid [9-isopropyp-1,2,3,4-tetrahaydro-1,4-methano-naphthalen-5-yl]-amide, and the isomers thereof. Mixtures of carboxanilide-type fungicidies can also be used.

Examples of carbamate type fungicides that are useful in the present invention include, without limitation, propamacarb and propamacarb hydrochloride. Mixtures of carbamate-type fungicidies can also be used.

Examples of anilinopyrimidine type fungicides that are useful in the present invention include, without limitation, cyprodnil, mepanipyrim and pyrimethanil. Mixtures of anilinopyrimidine-type fungicidies can also be used.

Examples of benzimidazole type fungicides that are useful in the present invention include, without limitation, benomyl, carbendazim, fuberidazole, and thiabendazole. Mixtures of benzimidazole-type fungicidies can also be used.

Examples of systemic type fungicides that are useful in the present invention include, without limitation, mefenoxam, metalaxyl-M, thiophanate-methyl, benalaxyl, cymoxanil, cyprofuram, furalaxyl, ofurace, oxadixyl, fosetyl-aluminium, phosphorous acid and its salts. Mixtures of systemic-type fungicidies can also be used.

Mixtures of fungicides are also contemplated. For example, and not for limitation, mixtures of systemic type fungicides in combination with benzimidazole-, anilinopyrimidine-, carbamate-, carboxanilide-, amide- and carboxamide-, phenylpyrrole-, strobilurin-, or triazole-type fungicides are contemplated by the present invention.

Preferred fungicides include metalaxyl, fludioxonil, azoxystrobin, myclobutanil, and difenconazole. Particularly preferred fungicides include fludioxonil.

The fast-drying liquid compositions of the present invention comprise a fungicidally effective amount of fungicide. More particularly, the fungicide is present in an amount from between about 1% to about 40% by weight of the total composition. Preferably, the fungicide is present in an amount from about 5% to about 30% by weight; about 5% to about 25%; about 5% to about 20%; about 5% to about 15%; about 5% to about 10% by weight. More preferably, the fungicide is present in an amount from about 6% to about 8% by weight.

Insecticides useful in the composition of the present invention include any agent useful for the prevention or treatment of damage caused by insect pests. Insecticides useful in the composition of the present invention include those classified as neonicotinoids, pyrethroids, phosphorus compounds, carbamates and others.

Examples of neonicotinoid insecticides that are useful in the present invention include, without limitation, acetamiprid, clothianidin, dinotefuran, imidacloprid, nitenpyram, thiacloprid, thiamethoxam. Preferred neonicotinoid insecticides include clothianidil, imidacloprid and thiamethoxam. Mixtures of neonicotinoid insecticides are also contemplated. Particularly preferred neonicotinoid insecticides include thiamethoxam and imidacloprid.

Pyrethroid insecticides useful in the composition of the present invention include, without limitation, alpha-cypermethrin, beta-cyfluthrin, beta-cypermethrin, bifenthrin, bioallethrin, bioresmethrin, cycloprothrin, cyfluthrin, cyhalothrin, cypermethrin, cyphenothrin, deltamethrin, empenthrin, esfenvalerate, fenpropatluin, fenvalerate, flucythrinate, flumethrin, gamma-cyhalothrin, imiprothrin, lambda-cyhalothrin, methothrin, metofluthrin, permethrin, phenothrin, prallethrin, resmethrin, tau-fluvalinate, tefluthrin, tetramethrin, theta-cypennethrin, tralomethrin, transfluthrin, and zeta-cypermethrin. Preferred pyrethroid insecticides include tefluthrin and lambda cyhalothrin. Mixtures of pyrethroid insecticides are also contemplated.

Phosphorus insecticides useful in the composition of the present invention include, without limitation, phorate, phosalone, phosmet, phosphamidon, phoxim. Mixtures of phosphorus insecticides are also contemplated.

Carbamate insecticides useful in the composition of the present invention include, without limitation, pirimicarb, benfuracarb, carbaryl, carbofuran, carbosulfan, ethiofencarb, fenobucarb, formetanate, furathiocarb, isoprocarb, methiocarb, methomyl, metolcarb, oxamyl, propoxur, trimethacarb, 3,5-xylyl methylcarbamate, and xylylcarb. Mixtures of carbamate insecticides are also contemplated.

Mixtures of the classes of insecticides are also contemplated. For example, and not for limitation, carbamate insecticides may be mixed with pyrethroid, neonicotinoid, or phosphorus insecticides; pyrethroid insecticides may be mixed with carbamate, neonicotinoid, or phosphorus insecticides; neonicotinoid insecticides may be mixed with pyrethroid, phosphorus or carbamate insecticides; phosphorus insecticides may be mixed with neonicotinoid, carbamate, or pyrethroid insecticides.

Insecticides are present in the fast-drying composition of the present invention in amounts ranging from about 5% to about 50% by weight. Preferably, insecticides are present in amounts ranging from about 20% to about 45% by weight; about 20% to about 40%; about 20% to about 35%. More preferably, insecticides are present in amounts from about 25% to about 30% by weight.

Wetting agents useful in the fast-drying composition of the present invention include, without limitation, one or more anionic surfactants, nonionic surfactants and zwitterionic surfactants.

Anionic surfactants include, without limitation, one or more of alcohol sulfates, alcohol ether sulfates, alkylaryl ether sulfates, alkylaryl sulfonates such as alkylbenzene sulfonates and alkylnaphthalene sulfonates and salts thereof, alkyl sulfonates, mono- or di-phosphate esters of polyalkoxylated alkyl alcohols or alkylphenols, mono- or di-sulfosuccinate esters of $C_{12}$-$C_{15}$ alkanols or polyalkoxylated $C_{12}$-$C_{15}$ alkanols, alcohol ether carboxylates, phenolic ether carboxylates, polybasic acid esters of ethoxylated polyoxyalkylene glycols consisting of oxybutylene or the residue of tetrahydrofuran, sulfoalkylamides and salts thereof such as N-methyl-N-oleoyltaurate Na salt, polyoxyalkylene alkylphenol carboxylates, polyoxyalkylene alcohol carboxylates alkyl polyglycoside/alkenyl succinic anhydride condensation products, alkyl ester sulfates, napthalene sulfonates, naphthalene formaldehyde condensates, alkyl sulfonamides, sulfonated aliphatic polyesters, sulfate esters of styrylphenyl alkoxylates, and sulfonate esters of styrylphenyl alkoxylates and their corresponding sodium, potassium, calcium, magnesium, zinc, ammonium, alkylammonium, diethanolammonium, or triethanolammonium salts, salts of ligninsulfonic acid such as the sodium, potassium, magnesium, calcium or ammonium salt, polyarylphenol polyalkoxyether sulfates and polyarylphenol polyalkoxyether phosphates, and sulfated alkyl phenol ethoxylates and phosphated alkyl phenol ethoxylates. Preferred anionic surfactants include, without limitation, N-methyl-N-oleoyltaurate Na salt; tristyrylphenol sulphate; ethoxylated lignin sulfonate; ethoxylated nonylphenol phosphate ester; calcium alkylbenzene sulfonate; ethoxylated nonylphenol phosphate ester; ethoxylated tridecylalcohol phosphate ester; lignosulfonic acid Na salt; and naphthalenesulfonic acid Na salt.

Non-ionic surfactants useful as wetting agents in the composition of the present invention include, without limitation, one or more polyarylphenol polyethoxy ethers, polyalkylphenol polyethoxy ethers, polyglycol ether derivatives of saturated fatty acids, polyglycol ether derivatives of unsaturated fatty acids, polyglycol ether derivatives of aliphatic alcohols, polyglycol ether derivatives of cycloaliphatic alcohols, fatty acid esters of polyoxyethylene sorbitan, alkoxylated vegetable oils, alkoxylated acetylenic diols, polyalkoxylated alkylphenols, fatty acid alkoxylates, sorbitan alkoxylates, sorbitol esters, $C_8$-$C_{22}$ alkyl or alkenyl polyglycosides, polyalkoxy styrylaryl ethers, alkylamine oxides, block copolymer ethers, polyalkoxylated fatty glyceride, polyalkylene glycol ethers, linear aliphatic or aromatic polyesters, organo silicones, polyaryl phenols, sorbitol ester alkoxylates, and mono- and diesters of ethylene glycol and mixtures thereof. Preferred non-ionic surfactants include one or more ethoxylated fatty alcohol; ethoxylated tristyrylphenol; ethoxylated lauryl alcohol; ethoxylated castor oil; ethoxylated nonylphenol.

Zwitterionic surfactants useful as wetting agents in the composition of the present invention include, without limitation, alkanol amides of $C_8$-$C_{18}$ fatty acids and $C_8$-$C_{18}$ fatty amine polyalkoxylates, $C_{10}$-$C_{18}$ alkyldimethylbenzylammonium chlorides, coconut alkyldimethylaminoacetic acids, and phosphate esters of $C_{8-18}$ fatty amine polyalkoxylates.

Dispersing agents, or emulsifying agents, useful in the composition of the present invention include, without limitation, alkyleneoxide random and block copolymers such as ethylene oxide-propylene oxide block copolymers (EO/PO block copolymers) including both EO-PO-EO and PO-EO-PO block copolymers; ethylene oxide-butylene oxide random and block copolymers; $C_{2-6}$ alkyl adducts of ethylene oxide-propylene oxide random and block copolymers; $C_{2-6}$ alkyl adducts of ethylene oxide-butylene oxide random and block copolymers; polyoxyethylene-polyoxypropylene monoalkylethers such as methyl ether, ethyl ether, propyl ether, butyl ether or mixtures thereof; vinylacetate/vinylpyrrolidone copolymers; alkylated vinylpyrrolidone copolymers; polyvinylpyrrolidone; and polyalkyleneglycol including the polypropylene glycols and polyethylene glycols. Preferred dispersing agents include copolymer butanol PO/EO and acrylic graft copolymer in water and propyleneglycole.

Drying agents useful in the composition of the present invention include, without limitation, one or more metal oxides such as silicon dioxide, titanium dioxide, aluminum oxide, zirconium oxide and fumed silica; and polymer wax, including oxidized and non-oxidized polyethylene wax, polyethylene copolymer wax, Montan wax, and polyether wax. Preferred drying agents are silicon dioxide and polyethylene wax.

Suberization agents useful in the composition of the present invention include, without limitation, one or more starches, alkyl triols, alkyl diols, phenolic polymers, aliphatic polymers, carboxylic acids, and dicarboxylic acids. Specific suberization agents include corn or potato starch, propane-1,2,3-triol, and octanoic acid.

The composition may further comprise formulation agents known in the art of pesticides. Such agents include, but are not limited to, antifreeze agents (such as but not limited to glycerine, ethylene glycol, propylene glycol, monopropylene glycol, hexylene glycol, 1-methoxy-2-propanol, cyclohexanol), buffering agents (such as but not limited to sodium hydroxide, phosphoric acid), biocides (such as but not limited to 1,2-benzisothiazolin-3-one), preserving agents (such as but not limited to derivatives of benzoic acid, sorbic acid, formaldehyde, a combination of methyl parahydroxybenzoate and propyl parahydroxybenzoate), stabilizing agents (such as but not limited to acids, preferably organic acids, such as dodecylbenzene sulfonic acid, acetic acid, propionic acid or butyl hydroxyl toluene, butyl hydroxyl anisole), thickening agents (such as but not limited to heteropolysaccharide and starches), pigments and colorants (such as but not limited to dyes, titanium dioxide), and antifoaming agents (such as but not limited to those based on silicone, particularly polydimethylsiloxane). Such additives are commercially available and known in the art.

When a liquid fungicide or insecticide is incorporated into the formulation, the formulation may optionally comprise a solvent. The solvent may be either water insoluble or slightly water soluble. Water insoluble solvents include, but are not limited to, isobornyl acetate, methyl oleate, aromatic solvents and mixtures thereof. Slightly water soluble solvents include, but are not limited to, 2-hepatonone, acetophenone, alcohols, ketones, and mixtures thereof.

Preferred fast-drying liquid formulations comprise about 20% to about 35% by weight thiamethoxam and about 5% to about 10% fludioxonil and the following components, by weight:
  a. about 1-5% at least one wetting agent;
  b. about 2-8% at least one dispersing agent;
  c. about 0.2-5.0% at least one drying agent;
  d. about 0.05-8.0% at least one suberization agent;
  e. about 12-18% at least one antifreeze.

More preferably, the fast-drying liquid formulations of the present invention comprise about 25% to about 30% thiamethoxam and about 6% to about 8% fludioxonil and the following components, by weight:
  a. about 1-5% at least one wetting agent;
  b. about 2-8% at least one dispersing agent;
  c. about 0.2-3.0% at least one drying agent;
  d. about 0.05-8.0% at least one suberization agent;
  e. about 12-18% at least one antifreeze.

The inventive compositions contain and/or may be applied together or sequentially with further active compounds. These further compounds can be fertilizers or micronutrient donors or other preparations that influence plant growth. They can also be selective herbicides, fungicides, other insecticides, bactericides, insect growth regulators, plant growth regulators, nematicides, molluscicides or mixtures of several of these preparations.

The liquid compositions of the present invention are useful in a method for preventing pest infestation in useful crops comprising treating plant propagation material, including seeds, with a pesticidally effective amount of the fast-drying liquid compositions.

Pests may include, without limitation, fungi, bacteria and insects. The composition of the present invention may be used to prevent infestation by fungi pathogens including *Pythium, Tilletia, Gerlachia, Septoria, Ustilago, Fusarium, Rhizoctonia*, Oomycetes such as *Phytophthora, Plasmopara, Pseudoperonospora, Bremia* and others, as well as against the *Botrytis* species, *Pyrenophora, Monilinia* and further representatives of the Ascomycetes, Deuteromycetes and Basidiomycetes classes.

Bacteria prevented and/or treated by application of the composition of the present invention includes, without limitation, *Erwinia, Cornybacterium, Enterobacter, Pectobacterium, Pantoea* or *Brenneria, Acinetobacter, Serratia, Lactobacilis*, and *Flavobacterium*.

The aqueous compositions of the invention are formulated for protecting cultivated plants and their propagation materials. The inventive compositions are advantageously formulated for seed treatment applications against fungi and soil inhabiting insects that can damage the crop in the early stages of plant development. For example and not for limitation, the compositions can be formulated to target insects and representatives of the order Acarnia including:

from the order Lepidoptera, for example, *Acleris* spp., *Adoxophyes* spp., *Aegeria* spp., *Agrotis* spp., Alabama argillaceae, *Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosina* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Tricboplusia ni* and *Yponomeuta* spp.;

from the order Coleoptera, for example, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., Scarabeidae, *Sitophilus* spp., *Sitotroga* spp., *Tenebrio* spp., *Tribolium* spp. and *Trogoderma* spp.; from the order Orthoptera, for example, *Blatta* spp., *Blattella* spp., *Gryllotalpa* spp., *Leucophaea maderae, Locusta* spp., eriplaneta spp. and *Schistocerca* spp.;

from the order Isoptera, for example, *Reticulitermes* spp.;
from the order Psocoptera, for example, *Liposcelis* spp.;
from the order Anoplura, for example, *Haematopinus* spp., *Linognatbus* spp., *Pediculus* spp., *Pemphigus* spp. and *Phylloxera* spp.;
from the order Mallophaga, for example, *Damalinea* spp. and *Trichodectes* spp.;
from the order Thysanoptera, for example, *Frankliniella* spp., *Hercinothrips* spp., *Taeniothrips* spp., *Thrips palmi, Thrips tabaci* and *cirtothrips aurantii;* from the order Heteroptera, for example, *Cimex* spp., *Distantiella theobroma*, *Dysdercus* spp., *Euchistus* spp., *Eurygaster* spp., *Leptocorisa* spp., *Nezara* spp., *Piesma* spp., *Rhodnius* spp., *Sahlbergella singularis*, *Scotinophara* spp. and *Triatoma* spp.;

from the order Homoptera, for example, *Aleurothrixus floccosus*, *Aleyrodes brassicae*, *Aonidiella* spp., Aphididae, *Aphis* spp., *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma larigerum*, *Erythroneura* spp., *Gascardia* spp., *Laodelphax* spp., *Lecanium corni*, *Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporaiiorum*, *Trioza erytreae* and *Unaspis citri*;

from the order Hymenoptera, for example, *Acromynnex*, *Atta* spp., *Cephus* spp., *Diprion* spp., Diprionidae, *Gilpinia polytoma*, *Hoplocampa* spp., *Lasius* spp., *Monomorium pharaonis*, *Neodiprion* spp., *Solenopsis* spp. and *Vespa* spp.;

from the order Diptera, for example, *Aedes* spp., *Antherigona soccata*, *Bibio hortulanus*, *Calliphora erythrocephala*, *Ceratitis* spp., *Chrysomyia* spp., *Culex* spp., *Cuterebra* spp., *Dacus* spp., *Drosophila melanogaster*, *Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis pomonella*, *Sciara* spp., *Stomoxys* spp., *Tabanus* spp., *Tannia* spp. and *Tipula* spp.;

from the order Siphonaptera, for example, *Ceratophyllus* spp. and *Xenopsylla cheopis*;

and from the order *Thysanura*, for example, *Lepisma saccharina*; and crucifer flea beetles (*Phyllotreta* spp.), root maggots (*Delia* spp.), cabbage seedpod weevil (*Ceutorhynchus* spp.) and aphids.

The term "plant propagation material" is used herein to refer to all the generative parts of the plant that can be used for the multiplication of the vegetative plant material such as cuttings and tubers (for example potatoes). There may be mentioned, for example and not for limitation, the seeds (in the strict sense), roots, fruits, tubers, bulbs, rhizomes, and parts of plants. Germinated plants and young plants, which are to be transplanted after germination or after emergence from the soil, may also be mentioned. These young plants may be coated before transplantation by a total or partial treatment by immersion or the like. In a specific embodiment, the method of the present invention has particular application for coating the plant propagation material of cultivated plants. Such plants are those plants that are cultivated by man, or from which is harvested parts or products that are used by man. Suitable cultivated plant propagation material includes, but is not limited to, seed selected from monocotyledonous, dicotyledonous, and multicotyledonous (gymnosperm) plants.

Specifically, plant propagation material includes seeds and cuttings and other generative parts of plants including tubers (such as but not limited to potatoes, Jerusalam artichokes and yams), bulbs (such as but not limited to onion, hyacinth, squill, amaryllis, snowdrop, tulip, daffodil, narcissis, lily and orchid), root vegetables (such as but not limited to carrots, beets, arrowhead, arrowroot, cassayas, Chinese artichoke, globe artichoke, horseradish, parsnips, radishes, and the like), trees, shrubs, and other ornamentals, including roses.

The liquid composition of the present invention may be used in a method for preventing pests, including fungi and insects, in cut seeds and propagation materials. For example and not for limitation, some planting regions cut seedling potatoes prior to planting, exposing the inner flesh of the seedling to the elements. Such exposure increases the risk of infection by fungi, bacteria, insects and other pests. The liquid composition of the present invention provides a barrier against these elements, preventing contamination of the seedling, thus resulting in reduced decay of the plant propagation materials.

The fast-drying liquid compositions of the present invention are exemplified by the following non-limiting examples.

EXAMPLE 1

Formulation

| Agent | Amount (wt. %) |
|---|---|
| Thiamethoxam | 28 |
| Fludioxonil | 7 |
| Naphthalenesulfonic acid, Na salt | 1.3 |
| Acrylic graft copolymer in water and propyleneglycole | 2 |
| Copolymer butanol PO/EO | 2 |
| Polydimethylsiloxane | 0.1 |
| Propylene glycol | 15 |
| Propane-1,2,3-triol (glycerine) | 5 |
| Phosphoric acid (85% solution) | 0.05-0.13 |
| Starch | 0.05 |
| Silicon dioxide | 0.4 |
| 1,2-benziosthiazolin-3-one | 0.4 |
| Heteropolysaccharide | 0.05-0.25 |
| NaOH (33% solution) | 0.02-0.04 |
| Water | Balance to 100% |

To a suitably sized vessel equipped with a Cowles mixer, charge the water and start agitation. Charge pre-heated (up to 50° C.) copolymer butanol PO/EO and agitate until homogeneous. Charge acrylic graft copolymer and agitate until homogeneous. Under a hood, charge naphthalenesulfonic acid sodium salt and agitate until homogeneous.

To this mixture under agitation, charge the polydimethylsiloxane, propylene glycol, glycerin, phosphoric acid, starch, and biocide, and mix until homogeneous.

Under a hood, charge thiamethoxam and fludioxonil to the water mixture under agitation. Silicon dioxide can either be added at this time, or post milling if product has been separately micronized. Mix for 15 minutes to half an hour. Check pH and adjust with sodium hydroxide solution if necessary (target pH in neat mixture is between 5.5-6.5). Using a high shear mixer (type Ross, Silverson or Ultra Turax), pre-grind the mixture until 95% of the particles are below 150 microns. Using a horizontal mill (type Dyno or Premier) charged between 80-85% of total volume with 1-2 mm glass or zirconium beads, mill the mixture under cooling system (temperature should not be higher than 35° C. during the entire process), until 50% of the particle is between 1.5-3.0 microns. Filtrate product through a 100 mesh sieve. Check pH and adjust if necessary with phosphoric acid and/or sodium hydroxide solutions until pH of neat mill base is between 5.5-6.5.

Separately, in a vessel with Cowles mixer, prepare a 2% heteropolysaccaride gel in water. Allow the gel to fully swell for several hours prior to use. To the mill base, add the amount of gel necessary to reach a final neat viscosity between 300-500 cPs. Filter final product through a 50 Mesh sieve.

EXAMPLE 2

Formulation

| Agent | Amount (wt. %) |
|---|---|
| Thiamethoxam | 28 |
| Fludioxonil | 7 |
| Lignosulfonic acid, Na salt | 2 |
| Acrylic graft copolymer in water and propyleneglycole | 2 |
| Copolymer butanol PO/EO | 2 |
| Propylene glycol | 15 |
| Propane-1,2,3-triol (glycerine) | 5 |
| Polydimethylsiloxane | 0.1 |
| Phosphoric acid (85% solution) | 0.05-0.13 |
| Starch | 0.05 |
| Polyethylene wax | 3.0 |
| 1,2-benziosthiazolin-3-one (biocide) | 0.4 |
| Heteropolysaccharide | 0.05-0.25 |
| NaOH (33% solution) | 0.0-0.02 |
| Water | Balance to 100% |

To a suitably sized vessel equipped with a Cowles mixer, charge the water and start agitation. Charge pre-heated (up to 50° C.) copolymer butanol PO/EO and agitate until homogeneous. Charge acrylic graft copolymer and agitate until homogeneous. Under a hood, charge lignosulfonic acid sodium salt and agitate until homogeneous.

To this mixture under agitation, charge the polydimethylsiloxane, propylene glycol, glycerin, phosphoric acid, starch, and biocide, and mix until homogeneous.

Under a hood, charge the thiamethoxam and fludioxonil to the water mixture under agitation. Polyethylene wax can either be added at this time, or post milling if product has been separately micronized. Mix for 15 minutes to half an hour. Check pH and adjust with sodium hydroxide solution if necessary (target pH in neat mixture is between 5.5-6.5). Using a high shear mixer (type Ross, Silverson or Ultra Turax), pre-grind the mixture until 95% of the particles are below 150 microns. Using an horizontal mill (type Dyno or Premier) charged between 80-85% of total volume with 1-2 mm glass or zirconium beads, mill the mixture under cooling system (temperature should not be higher than 35° C. during the entire process), until 50% of the particles are between 1.5-3.0 microns. Filtrate product through a 100 mesh sieve. Check pH and adjust if necessary with phosphoric acid and/or sodium hydroxide solutions until pH of neat millbase is between 5.5-6.5. Separately, in a vessel with Cowles mixer, prepare a 2% heteropolysaccaride gel in water. Allow the gel to fully swell for several hours prior to use. To the mill base, add the amount of gel necessary to reach a final neat viscosity between 300-500 cPs. Filter final product through a 50 mesh sieve.

The liquid compositions of the present invention are fast-drying compared to other liquid treatments for plant propagation materials. The compositions of the present invention dry in periods between about 30 minutes and 200 minutes. Preferably, the liquid compositions of the present invention dry after application in periods between about 60 minutes to about 180 minutes. More preferably, the post-application drying time of the liquid compositions of the present invention is between about 75 minutes to about 90 minutes.

The following non-limiting examples demonstrate the decreased drying time of the liquid compositions of the present invention.

EXAMPLE 3

Drying Time

Drying times of the liquid compositions of the present invention were compared to existing liquid treatments for plant propagation materials. Specifically, compositions of the present invention were compared to (a) a liquid formulation of fludioxonil (Maxim® 4FS) and (b) a powder formulation of fludioxonil in combination with mancozeb (Maxim® MZ).

Potato tubers of approximately 5 $cm^3$ were treated with liquid compositions of the present invention and with fludioxonil formulations known in the art (Maxim® 4FS and Maxim® MZ). Using a recommended application rate/100 kg tubers and adjusting to constant total volume for all treatments (0.626 g slurry/0.5 kg tubers), the liquid composition was added to a treatment bag, the cut potato tubers were added, and the bag was shaken for about 15 seconds. The tubers were then removed and allowed to dry at ambient temperature. The results are provided below.

| Composition | Observations | Drying time (minutes) |
|---|---|---|
| Example 1 | Good coverage; homogeneous | 75-90 |
| Example 2 | Good coverage; homogeneous | 90 |
| Example 2 (without polyethylene wax) | Fairly good coverage of tubers | >150 |
| Maxim ™ 4FS (Syngenta) | Fairly good coverage of tubers | >150 |
| Maxim ™ MZ* (Syngenta) | Very unhomogeneous on tubers; all product on cut side, none on skin | 60** |

*applied dry as dust treatment
**already dry after 60 minutes, but product flakes off tuber when touched The following non-limiting examples demonstrate the reduction in decay of three different types of potato seedlings.

EXAMPLE 4

Fungal Decay

Using the formulation described above in Example 1, labelled A14382, different types of cut potato seedlings were treated and tested for *Fusarium* decay against untreated control (UTC), and a liquid formulation of fludioxonil, Maxim™ 4FS (Syngenta). Each variety included all three treatments.

For each variety, seed was cut and treated on seven (7) different treatment days. These included the day of planting (0 days), 2, 5, 7, 9, 12, and 14 days before planting. After being cut, the seed was stored in burlap bags at 50° F. and 90% relative humidity until the planting date, except for the last treatment day in which the seed was cut, treated, and planted on the same day.

All of the seed was inoculated the day of planting with a slurry of *Fusarium sambucinum* isolate FID 71-6 (Benzimidazol sensitive), *F. sambucinum* isolate FID 212 (Benzimidazol resistant), and *F. solani* var. *coeruleum* isolate MR-6. 4.2 ml of water suspension at $1.6 \times 10^4$ CFU/ml was applied to 48 seed pieces for each treatment.

Data reported here are 7 or 9 days before planting. Data collected here shows early season field evaluations where the plants were dug up and evaluated for seed piece decay. Seed piece decay was evaluated in percentage of *Fusarium* "dry" decay, soft rot decay, or a combination of the two in each seed piece, as well as percentage of all of the seed pieces in each treatment which have decay.

Russet Burbank
DESTRUCTIVE SAMPLING-"DRY ROT"

|  | % Dry Rot 7-Day |
| --- | --- |
| RB Untreated | 3.85 |
| RB Maxim 4FS | 0.58 |
| RB Example 1 | 0.03 |

DESTRUCTIVE SAMPLING-"DRY ROT" INCIDENCE (% OF SEED PIECES WITH ROT PER TREATMENT)

|  | % Dry Rot Incidence 7-Day |
| --- | --- |
| RB Untreated | 12.50 |
| RB Maxim 4FS | 7.50 |
| RB Example 1 | 2.50 |

DESTRUCTIVE SAMPLING-SOFT ROT

|  | % Soft Rot 7-Day |
| --- | --- |
| RB Untreated | 7.38 |
| RB Maxim 4FS | 0.25 |
| RB Example 1 | 0.00 |

DESTRUCTIVE SAMPLING-SOFT ROT INCIDENCE (% OF SEED PIECES WITH ROT PER TREATMENT)

|  | % Soft Rot Incidence 7-Day |
| --- | --- |
| RB Untreated | 10.00 |
| RB Maxim 4FS | 2.50 |
| RB Example 1 | 0.00 |

Nordonna
DESTRUCTIVE SAMPLING-DRY ROT

|  | % Dry Rot 7-Day |
| --- | --- |
| N Untreated | 1.73 |
| N Maxim 4FS | 0.50 |
| N Example 1 | 0.33 |

DESTRUCTIVE SAMPLING-DRY ROT INCIDENCE (% OF SEED PIECES WITH ROT PER TREATMENT)

|  | Dry Rot Incidence 7-Day |
| --- | --- |
| N Untreated | 12.50 |
| N Maxim 4FS | 5.00 |
| N Example 1 | 5.00 |

DESTRUCTIVE SAMPLING-SOFT ROT

|  | % Soft Rot 7-Day |
| --- | --- |
| N Untreated | 3.00 |
| N Maxim 4FS | 2.50 |
| N Example 1 | 1.38 |

DESTRUCTIVE SAMPLING-SOFT ROT INCIDENCE (% OF SEED PIECES WITH ROT PER TREATMENT)

|  | Soft Rot Incidence 7-Day |
| --- | --- |
| N Untreated | 5.13 |
| N Maxim 4FS | 2.50 |
| N Example 1 | 0.00 |

FL1833
DESTRUCTIVE SAMPLING-DRY ROT

|  | % Dry Rot 9-Day |
| --- | --- |
| FL Untreated | 9.95 |
| FL Maxim 4FS | 0.48 |
| FL Example 1 | 0.25 |

DESTRUCTIVE SAMPLING-DRY ROT INCIDENCE (% OF SEED PIECES WITH ROT PER TREATMENT)

|  | Dry Rot Incidence 9-Day |
| --- | --- |
| FL Untreated | 55.00 |
| FL Maxim 4FS | 10.00 |
| FL Example 1 | 2.50 |

DESTRUCTIVE SAMPLING-SOFT ROT

|  | % Soft Rot 9-Day |
| --- | --- |
| FL Untreated | 2.50 |
| FL Maxim 4FS | 0.00 |
| FL Example 1 | 0.00 |

DESTRUCTIVE SAMPLING-SOFT ROT INCIDENCE (% OF SEED PIECES WITH ROT PER TREATMENT)

|  | Soft Rot Incidence 9-Day |
| --- | --- |
| FL Untreated | 2.50 |
| FL Maxim 4FS | 0.00 |
| FL Example 1 | 0.00 |

Cut seedlings undergo a process of self-healing, called suberization. During suberization, the cell walls of the seedling excrete suberin, a biochemical that protects the cut area by forming a cork-like barrier between the environmental elements and the inner flesh of the seed. Suberin is composed of two distinctly different biochemical components: a polyphenolic component and a polyaliphatic component. Once the plant material experiences a trauma, which includes cutting and bruising, the plant's own cells initiate suberization to form the protective, healing coating.

As shown in Example 4, the fast-drying formulation of the present invention promotes the cut tuber's natural suberization process, allowing the self-protecting coating to protect the cut, or other trauma cite, and fight against external pathogens. Accordingly, the present invention further provides a process for promoting suberization in plant propagation material comprising applying to the propagation material an effective amount of the liquid composition described herein.

EXAMPLE 5

Suberization

Suberization is objectively measured using a process called the "suberization index." The following protocol is used to obtain the measurements.

Eight seed pieces from each treatment are removed for evaluation at 2, 3, 6, 8 and 13 days after cutting and treating.

A rectangular block of tissue, approximately 1×3×0.5 cm, is cut from each seed piece at the center of the juncture of the two cut planes. Under a dissecting scope, three serial sections approximately 1 mm in thickness are cut from each rectangular block of tissue. The outer-most sections are discarded and the other two sections are mounted in water on a microscope slide.

The sections are evaluated on a phase contrast microscope using both incandescent and ultraviolet light.

All measurements are taken at 100× magnification, at which 10 units are equal to 0.08 mm.

Evaluations include measurements and observations of the number of cell layers and the thickness of the suberized cells, the uniformity of the suberin development across the cut surface, the inception and development of a meristematic region (phellogen) and the periclinal cell division which forms the phellogen, the final stage of the healing process. These measurements are all used to calculate the "suberization index".

EXAMPLE 6

Selective Loading

Generally, treatment of potato tubers and/or cut seeds with liquid pesticides results in the majority of the pesticide settling on the cut side of the seed rather than on the skin side of the seed. Such affinity for the cut side is thought to be based on the pesticides' affinity for water. Because of the naturally-occurring suberization of the tuber or seed, the cut surface is believed to provide better protection against pests and does not need as much pesticide. Rather, the pesticidal action is more useful on the skin side of the tuber, where the eyes are present and where germination occurs.

The formulation of the present invention demonstrates a tendency to selectively load the pesticide on the skin side of the tuber. Although not wanting to be bound by any particular theory, it is thought that the nonpolar nature of the waxes and silicas present in the formulations of the present invention have affinity for the skin side, causing a greater loading of the active ingredients on the skin side. Such affinity is demonstrated by the following results, wherein the thiamethoxam/fluidioxonil formulation of Example 2 of the present invention is compared with the same formulation of Example 2 without wax.

|  | Fludioxonil | Example 2 | | Example 2 w/o wax | | Fludioxonil + Mancozeb |
|---|---|---|---|---|---|---|
|  |  | Fludioxonil | thiamethoxam | Fludioxonil | thiamethoxam |  |
| Cut side | 21 | 4 | 20 | 4 | 20 | 13 |
| Skin side | 21 | 5 | 21 | 5 | 13 | 10 |

As shown in the table above, the amount of thiamethoxam present on the cut side of the tuber is essentially the same for either formulation; however, the selectivity of the ibiamethoxam for the skin side is more defined for the wax-containing formulation. Additionally, the amount of fludioxonil present on the skin side of the tuber is greater than that of the cut side.

EXAMPLE 6

Insect Protection

Comparative trials were conducted to show the protection of the formulation described herein against different insect pests.

In two trials measuring the control of Colorado Potato Beetles on potatoes, the formulation of Example 1 showed improved control versus the untreated check and slightly better control than or the same control as imidacloprid.

| % Defoliation | Untreated | Imidacloprid | Example 1 |
|---|---|---|---|
| 102 days after planting (Wash. State) | 77.5 | 9 | 7.8 |
| 105 days after planting (Idaho) | 63.8 | 0 | 0 |

In trials testing the number of Green Peach Aphids per sample of potatoes, the formulation of Example 1 showed greater reduction in the number of aphid pests than the untreated check or Tops MZ Gaucho™ (Bayer Crop Science; imidacloprid formulation). Results are measured as aphids per sample.

| Days after Planting | No Seed Treatment | Tops MZ Gaucho | Example 1 |
|---|---|---|---|
| 62 | 8.5 | 0 | 0 |
| 68 | 15 | 0.08 | 0.5 |
| 75 | 34 | 4 | 1 |
| 82 | 43 | 18 | 3.3 |
| 89 | 2.5 | 0.5 | 0 |

EXAMPLE 7

Improved Yield

The formulation of the present invention has shown improved yields on trials of potato crops. In trials conducted in Washington and Idaho, the crops resulting from potato seeds treated with the formulation of Example 1 showed better yield, as measured by plant stand, than the untreated control and better or comparable yield when compared to Tops MZ Gaucho (Bayer Crop Science).

| Percent Plant Stand | Untreated | Tops MZ Gaucho | Example 1 |
|---|---|---|---|
| Washington | 382 | 416 | 435 |
| Idaho | 243 | 364 | 342 |

The invention as set forth herein solves a problem known to exist in the art. As various changes could be made to the above composition and processes without departing from the scope of the invention, it is intended that all matter contained in this description shall be interpreted as illustrative only without limiting the scope of the present invention.

We claim:

1. A liquid composition for treating plant propagation material comprising water, an effective amount of active ingredients containing at least one fungicide and at least one insecticide, and a blend of the following components, by weight:
    a. about 0.05-20% at least one wetting agent;
    b. about 0.05-10% at least one dispersing agent;
    c. about 0.05-5% at least one drying agent;
    d. about 0.01-20% at least one suberization agent; and optionally,
    e. about 0-20% antifreeze; and optionally
    f. about 0-20% solvent
wherein the composition dries within 90 minutes of application to the plant propagation material.

2. The composition according to claim 1, wherein the fungicide is selected from fludioxonil, difenconazole, mefenoxam, azoxystrobin, trifloxystrobin, propiconazole, myclobutanil, captan, thiram, carboxin, oxycarboxin, imazalil, tebuconazole, mancozeb, maneb, pentachloronitrobenzene, streptomycin, thiabendazole, thiophanate-methyl, and triadimenol.

3. The composition according to claim 2, wherein the fungicide is fludioxonil.

4. The composition according to claim 1, wherein the insecticide is selected from acetamiprid, clothianidin, dinotefuran, imidacloprid, nitenpyram, thiacloprid, and thiamethoxam.

5. The composition according to claim 4, wherein the insecticide is thiamethoxam.

6. The composition according to claim 1, wherein the dispersing agent is one or more of copolymer butanol PO/EO and acrylic graft copolymer in water and propyleneglycole.

7. The composition according to claim 1, wherein the drying agent is one or more of inorganic oxides or polymer wax.

8. The composition according to claim 7, wherein the drying agent is an inorganic oxide.

9. The composition according to claim 8, wherein the drying agent is selected from silicon dioxide, titanium dioxide, aluminum oxide, zirconium oxide and fumed silica.

10. The composition according to claim 9, wherein the drying agent is silicon dioxide.

11. The composition according to claim 7, wherein the drying agent is a polymer wax selected from oxidized and non-oxidized polyethylene wax, polyethylene copolymer wax, Montan wax, and polyether wax.

12. The composition according to claim 11, wherein the polymer wax is polyethylene wax.

13. The composition according to claim 1, comprising water, thiamethoxam, fludioxonil, and the following components, by weight:
    a. about 1-5% at least one wetting agent;
    b. about 2-8% at least one dispersing agent;
    c. about 0.2-1.0% at least one drying agent;
    d. about 3-8% at least one suberization agent; and optionally,
    e. about 12-18% at least one antifreeze.

14. A method for promoting suberization in plant propagation material comprising treating the material with an effective amount of a composition according to claim 1.

15. Plant propagation material treated with the composition according to claim 1.

16. Plant propagation material treated with the composition according to claim 13.

17. A liquid composition for treating plant propagation material comprising water, fludioxonil, thiamethoxam, and a blend of the following components, by weight;
    a. about 0.05-20% of naphthalenesulfonic acid sodium salt;
    b. about 0.05-10% of one or more copolymer butanol PO/EO and acrylic graft copolymer in water and propyleneglycole;
    c. about 0.05-5% of silicon dioxide;
    d. about 0.01-20% of one or more propane-1,2,3-triol and starch; and optionally
    e. about 0-20% of propylene glycol.

18. A method for promoting suberization in plant propagation material comprising treating the material with an effective amount of a composition according to claim 17.

19. Plant propagation material treated with the composition according to claim 17.

20. A liquid composition for treating plant propagation material comprising water, fludioxonil, thiamethoxam, and a blend of the following components, by weight;
    a. about 0.05-20% of lignosulfonic acid sodium salt;
    b. about 0.05-10% of one or more copolymer butanol PO/EO and acrylic graft copolymer in water and propyleneglycole;
    c. about 0.05-5% of polyethylene wax;
    d. about 0.01-20% of one or more propane-1,2,3-triol and starch; and optionally
    e. about 0-20% of propylene glycol.

21. A method for promoting suberization in plant propagation material comprising treating the material with an effective amount of a composition according to claim 20.

22. Plant propagation material treated with the composition according to claim 20.

* * * * *